| United States Patent [19]
Bost et al.

[11] 3,943,179
[45] Mar. 9, 1976

[54] HYDROXYLATION OF AROMATIC COMPOUNDS

[75] Inventors: Pierre-Etienne Bost; Michel Costantini, both of Lyon; Michel Jouffret, Francheville le bas; Guy Lartigau, Lyon, all of France

[73] Assignee: Rhone-Poulenc Textile, Paris, France

[22] Filed: Sept. 27, 1973

[21] Appl. No.: 401,172

[30] Foreign Application Priority Data
Sept. 28, 1972 France .............................. 72.34358

[52] U.S. Cl. ......... 260/621 G; 260/613 D; 260/625
[51] Int. Cl.² .................. C07C 41/00; C07C 37/00
[58] Field of Search ........ 260/613 D, 621 G, 624 R, 260/625

[56] References Cited
UNITED STATES PATENTS

| | | | |
|---|---|---|---|
| 2,437,648 | 3/1948 | Milas .......................... | 260/621 G X |
| 2,792,430 | 5/1957 | Porter et al. .................. | 260/621 G |
| 2,903,480 | 9/1959 | Toland ........................ | 260/621 G X |
| 3,652,597 | 3/1972 | Bader et al. ................. | 260/621 G X |

*Primary Examiner*—Norman Morgenstern
*Attorney, Agent, or Firm*—Cushman, Darby & Cushman

[57] ABSTRACT

Phenols and phenol ethers are hydroxylated with hydrogen peroxide in the presence of sulphur, selenium, tellurium, phosphorus, arsenic or antimony. High yields of dihydric materials are obtained by this process which avoids the need to use peracids or very strong acids.

7 Claims, No Drawings

HYDROXYLATION OF AROMATIC COMPOUNDS

The present invention relates to the hydroxylation of aromatic compounds.

Numerous processes have been described for the oxidation of phenols and phenol ethers with hydrogen peroxide together with metal salts or with organic peracids (formed from hydrogen peroxide and a carboxylic acid). Depending on the particular case, it is possible using these processes to introduce a hydroxyl radical into the ring of the aromatic compound or to bring about oxidation of this ring in varying degrees, ranging from the production of quinones to the opening of the benzene ring with formation of degradation products: See A. CHWALA et al., J Prakt. Chem., 152, 46 (1939); G. G. HENDERSON, J. Chem. Soc., 91, 1659 (1910); S. L. FRIESS et al., J Chem. Soc., 74, 1305 (1952); H. FERNOLZ, Ber., 87, 578 (1954); H. DAVIDGE et al., J. Chem. Soc., 1958, 4569; and J. D. McCLURE et al., J. Org. Chem., 27 627 (1962). However, either because of low productivity of hydroxylation products (entailing the use of large amounts of reagents) or because of insufficient yields, none of the processes described above is of industrial value, particularly for the preparation of diphenols such as hydroquinone and pyrocatechol or of alkoxyphenols such as guaiacol and p-methoxyphenol.

Other processes of great industrial value have also been proposed for the hydroxylation of phenols and their ethers. Thus French Pat. Specification No. 1,479,354 describes a process for the preparation of hydroquinone and pyrocatechol by hydroxylation of phenol with an aliphatic peracid (especially performic acid), the degree of conversion of the phenol being limited to 30% at most. The best yields of diphenols relative to the hydrogen peroxide employed are obtained when the reaction is carried out in the presence of phosphoric acid (this yield then reaches a value of 73.5% for a degree of conversion of phenol of 8.7%). By replacing phosphoric acid by a mixture of pyrophosphoric acid and phosphorus pentoxide, Y. OGATA et al., C.A. 74, 76,134 obtained similar results.

Although these processes have a certain industrial value and represent obvious technical progress over those proposed previously, means have been sought to improve them by carrying out the direct hydroxylation of aromatic compounds with hydrogen peroxide alone by a process which avoids the formation of an organic peracid.

For this purpose, it has been proposed in French Pat. Specification No. 2,071,464 that the hydrogen peroxide/organic acid/phosphoric acid hydroxylation system be replaced by hydrogen peroxide in the presence of traces of a strong acid with a pK in water less than −0.1 and preferably of an agent which complexes any metal ions that may be present in the medium. Orthophosphoric and polyphosphoric acids (for example, pyrophosphoric acid) may be used as complexing agents. It has now been found, unexpectedly, that it is possible to carry out the hydroxylation of aromatic compounds by means of hydrogen peroxide without the need for the presence of strong acids with a pK in water less than −0.1, when certain metalloids from groups 5a and 6a of the Periodic Classification of the Elements (compare Handbook of Chemistry, 45th ed., page B-2) are used in conjunction with hydrogen peroxide.

The present invention provides a process for the hydroxylation of an aromatic compound of the general formula:

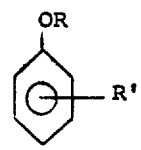

in which R and R' which may be identical or different each represent hydrogen or an alkyl radical, containing 1 to 4 carbon atoms, by treating the aromatic compound with hydrogen peroxide, in the presence of at least one metalloid which is sulphur, selenium, tellurium, phosphorus, arsenic or antimony.

Of these various metalloids, sulphur, selenium or phosphorus are used preferentially. Sulphur is particularly suitable.

In the above formulae each of R and R' can be for example a methyl, ethyl, propyl or butyl radical.

The amount of metalloid used expressed in gram atoms per mol of hydrogen peroxide can vary within quite wide limits. It is possible to use 0.001 to 1 gram atom of metalloid per mol of $H_2O_2$, and preferably 0.01 to 0.2 gram atom per mol.

The metalloid is used in the form of powder, the dimensions of the particles of which can vary.

The amount of hydrogen peroxide used can generally be of the order of one molecule of $H_2O_2$ per molecule of aromatic compound; it is, however, preferable not to exceed 0.3 mol of $H_2O_2$ per mol of aromatic compound, and more precisely 0.15 mol per mol of aromatic compound.

The concentration of the aqueous solution of hydrogen peroxide employed is generally not critical. Aqueous solutions of hydrogen peroxide of concentration greater than 20% by weight are suitable.

The process according to the invention can be carried out at temperatures of between 20° and 150°C, and preferably between 50° and 120°C, and at pressures greater than or equal to atmospheric pressure.

It has been found that the presence of metal ions of transition metals (Fe, Cu, Cr, Co, Mn, and V) in the reaction mixture has a detrimental effect on the way in which the hydroxylation takes place; it is thus preferable to inhibit the action of these metals, introduced either by the reagents or by the equipment, by working in the presence of complexing agents, which are stable towards hydrogen peroxide and give complexes which cannot be decomposed under the conditions of the reaction and in which the metal can no longer exert chemical activity. It is of little consequence whether the complexing agents lead to complexes which are soluble or insoluble in the medium. The ligand or ligands used are chosen as according to the metals present by means of simple experiments for each particular case. Phosphoric acids such as orthophosphoric acid and condensed phosphoric acids (pyrophosphoric acid; metaphosphoric acid and its polymers and polyphosphoric acids) and their acid esters are examples of complexing agents which are preferably used. Acid phosphates, which can be used include monoalkyl or dialkyl orthophosphates (methyl or dimethyl phosphate; ethyl or diethyl phosphate); monocyclohexyl or dicyclohexyl orthophosphates; monoaryl or diaryl orthophosphates (monophenyl or diphenyl orthophosphate); monoalkyl or dialkyl pyrophosphates or monoarylalkyl or diarylalkyl pyrophosphates (methyl pyrophosphate; diethyl pyrophosphate; or benzyl or dibenzyl pyrophosphate).

The amount of complexing agent introduced into the reaction mixture depends on its metal ion content. There is obviously no critical upper limit, it being possible for the amount of complexing agent to be in large excess relative to the amount necessary to complex the metals present. An amount representing 0.0001 to 5% by weight of the reaction mixture is generally very suitable.

The reaction can be carried out in the presence of inert organic solvents such as, for example, 1,2-dimethoxyethane, chloroform, acetonitrile, and dichloroethane, particularly when the temperature chosen is below the melting point of the aromatic compound.

Examples of aromatic compounds which can be hydroxylated by the process of the invention include phenol, cresols, anisole and phenetole. The process claimed can easily be carried out continuously.

The following Examples illustrate the invention.

EXAMPLE 1

94 g of phenol (1 mol), 0.2 g of pyrophosphoric acid and 0.32 g of sulphur (0.01 gram atom) are placed in a 250 cm³ three-necked flask equipped with a central stirrer, a condenser and a dropping funnel. The mixture is heated at 75°C, and then 2.6 g of 70% W/W $H_2O_2$ (0.0535 mol) are added. After heating for 1 hour, all the hydrogen peroxide has disappeared. 1.4 g of hydroquinone and 3 g of pyrocatechol are measured by gas-liquid chromatography.

The yield of hydroquinone relative to the hydrogen peroxide employed is 25.4% and the yield of pyrocatechol is 54.6% (corresponding to an overall yield of diphenols of 80%).

EXAMPLES 2 and 3

Example 1 was repeated, replacing the sulphur by phosphorus and selenium. The results given in the following table were obtained:

| Ex. | Metalloids | Duration | Unconverted $H_2O_2$, % of the original amount | Yield of hydroquinone relative to $H_2O_2$ employed | Yield of pyrocatechol relative to $H_2O_2$ employed |
|---|---|---|---|---|---|
| 2 | Red P | 3 hrs. | 14 % | 8 % | 18.2 % |
| 3 | Se | 1 hr. | 6 % | 17 % | 25 % |

We claim:
1. A process for the hydroxylation of an aromatic compound of the general formula:

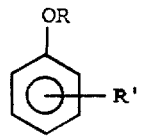

in which R and R', which may be identical or different, each represent a hydrogen atom or an alkyl radical containing 1 to 4 carbon atoms, wherein the aromatic compound is treated with hydrogen peroxide at a temperature from 20° to 150°C. in the presence of at least one element which is sulphur, selenium, tellurium, phosphorus, arsenic or antimony, in an amount from 0.001 to 1 gram atom of element per mol of hydrogen peroxide, the molar ratio of hydrogen peroxide to aromatic compound being not greater than 0.3:1.

2. A process according to claim 1 wherein the reaction is carried out in the presence of 0.01–0.2 gram atom of powdered sulphur, selenium or phosphorus.

3. A process according to claim 1 wherein the reaction is carried out in the presence of a phosphoric acid or an alkyl or aryl ester thereof.

4. A process according to claim 3, wherein the reaction is carried out in the presence of orthophosphoric or a condensed phosphoric acid or an alkyl or aryl acid ester thereof.

5. A process according to claim 3, wherein the phosphoric acid or alkyl or aryl ester thereof is used in an amount of 0.0001 to 5% by weight of reaction mixture.

6. A process according to claim 1 wherein the molar ratio of hydrogen peroxide to the aromatic compound is not greater than 0.15:1.

7. A process according to claim 1, wherein the aromatic compound is phenol.

* * * * *